United States Patent [19]
Nielsen et al.

[11] Patent Number: 5,244,763
[45] Date of Patent: Sep. 14, 1993

[54] POLYMERIC SCAVENGERS FOR OXIDIZED DEVELOPING AGENTS AND PHOTOGRAPHIC ELEMENTS CONTAINING THE SAME

[75] Inventors: Ralph B. Nielsen, Rochester; Lan B. Thai, Penfield; Hwei-ling Yau, Rochester, all of N.Y.

[73] Assignee: Eastman Kodak Company, Rochester, N.Y.

[21] Appl. No.: 3,038

[22] Filed: Jan. 11, 1993

Related U.S. Application Data

[62] Division of Ser. No. 740,732, Aug. 6, 1991, Pat. No. 5,198,517.

[51] Int. Cl.$^5$ .................. G03C 1/73; C08F 216/10; C08F 230/04; C08F 230/08; C08F 228/02; C08F 220/54

[52] U.S. Cl. .................................. 430/72; 526/240; 526/279; 526/287; 526/306; 526/307.2; 526/313

[58] Field of Search ................................ 430/72

[56] References Cited

U.S. PATENT DOCUMENTS 4,833,211  5/1989  Roggero et al. ............. 525/333.3

FOREIGN PATENT DOCUMENTS 0240843  10/1987  European Pat. Off. .

Primary Examiner—Joseph L. Schofer
Assistant Examiner—Wu C. Cheng
Attorney, Agent, or Firm—Robert A. Gerlach

[57] ABSTRACT

Reducing agents for oxidized developing agents and light sensitive elements containing the reducing agents wherein the reducing agents comprise a polymer having gallic acid or gallic acid derivative moieties.

29 Claims, No Drawings

POLYMERIC SCAVENGERS FOR OXIDIZED DEVELOPING AGENTS AND PHOTOGRAPHIC ELEMENTS CONTAINING THE SAME

This is a Divisional of application Ser. No. 740,732, filed Aug. 6, 1991 now U.S. Pat. No. 5,198,517.

BACKGROUND OF THE INVENTION

Field of the Invention

This invention relates to polymeric reducing agents for oxidized developing agents and to silver halide photographic elements containing such reducing agents for oxidized developing agents.

It is known in the art to add reducing agents (hereinafter called scavengers or $D_{ox}$ scavengers) for oxidized developing agent (hereinafter called $D_{ox}$) to photographic elements in order for the scavenger to interact with the oxidized developing agent and prevent it from reacting at an undesired location or at an undesired point in time. These scavengers have two primary applications. One use is in interlayers (i.e. a non-imaging layer between two imaging layers), where the scavenger decreases or eliminates wrong-color image formation caused by $D_{ox}$ migration between layers of different colors. The second use of such scavengers is in image-forming layers where the compounds function to reduce stain in areas of low dye formation (i.e. in the $D_{min}$). In this use, the scavenger can also control the characteristic curve shape of the film and improve granularity in multilayer systems. When coated in emulsion layers, the scavengers are referred to as competitors, because they compete with the image-forming compounds in the reaction with oxidized developing agent. In general, the requirements for an effective competitor are more demanding than for an effective interlayer scavenger.

A satisfactory scavenger has the following characteristics:
1) has high activity toward oxidized developer.
2) does not form colored products (stain) after reaction with oxidized developer.
3) has no unwanted interactions with other film components such as image-forming compounds or dyes.
4) can be easily coated in photographic layers.
5) does not crystallize in the coating solution during the coating process or in the film. Crystallization can lead to coating defects and reduced or variable activity.
6) remains immobile in the layer in which it is coated during the coating process, during the ageing of the film, and during the image development process.
7) is stable during the natural ageing of the film.
8) does not directly affect the sensitivity or development of silver halide emulsions.
9) can be easily manufactured.

Of this list, requirements 1, 3, and 8 are more critical for the use of a scavenger as a competitor than as an interlayer scavenger. One reason for this is that the competitor is coated directly with silver halide and other film components such as dye-forming compounds. Also, in order to reduce $D_{min}$ stain, the competitor must have higher reactivity toward $D_{ox}$ than the dye-image forming compound. In comparison, an interlayer scavenger of lower activity may function effectively as an interlayer scavenger as long as it can reduce $D_{ox}$ before it diffuses through the entire interlayer.

The use of substituted hydroquinone scavengers is well-known. Specific examples of the uses and various types of hydroquinones are disclosed in U.S. Pat. Nos. 2,243,294, 2,360,290, 2,403,721, 2,728,659, 2,732,300, 3,700,453, 4,198,239, 4,732,845, and West German OLS 2,149,789.

Polymeric scavengers which incorporate hydroquinone structures have been described in U.S. Pat. Nos. 4,345,016 and 4,983,506. Ballasted sulfonamidophenol and disulfonamidophenol scavengers have been described in U.S. Pat. Nos. 4,366,226 and 4,205,987, and in Research Disclosure 15162, November 1976. U.S. Pat. Nos. 4,474,874, 3,457,079, 4,476,219, and European Patent Application 115,305 disclose scavengers which are ballasted gallic esters and amides.

These scavenger compounds described above are generally hydrophobic and crystalline. They are introduced into photographic materials by the various known dispersion methods. These include oil-in-water dispersions, which are prepared by dissolving the compound in a high-boiling organic solvent together with a low-boiling solvent, and emulsifying the resulting solution with an aqueous gelatin solution containing a surfactant. The low-boiling organic solvent may then be removed by evaporating with heat under low pressure or by washing the dispersion with chilled water if the solvent is water-miscible. Other dispersion methods include dispersion in a latex, alkali dispersions, and solid microcrystalline dispersions. The dispersion process is labor-intensive and can introduce photographic variability, the added organic solvent increasing the total thickness of the film layers as well as possibly causing environmental problems because of the presence of solvents. Many ballasted compounds have a tendency to crystallize in the dispersion, severely affecting photographic performance, while the less hydrophobic compounds tend to diffuse between layers in the photographic packages.

Most of the scavengers described above are deficient in one or more of the requirements previously described for a satisfactory scavenger. Many ballasted hydroquinones have low or moderate activity toward oxidized developer and are unstable toward aerial oxidation during the natural ageing of photographic elements. This instability also leads to the formation of by-products which can fog silver halide emulsions. Disulfonamidophenol compounds are known to form a substantial yellow stain upon reaction with oxidized developing agents. Many of the compounds, including many gallic esters and amides, tend to crytallize after dispersion in a photographic element.

SUMMARY OF THE INVENTION

The invention provides a satisfactory reducing agent for oxidized developing agents and pertains to photographic light-sensitive elements containing the reducing agent. We have found that an active scavenger, which is non-staining, resistant to aerial oxidation and immobile in a photographic element, can be achieved by a polymer comprising at least 1 mol. % of a repeating unit represented by the formula (I):

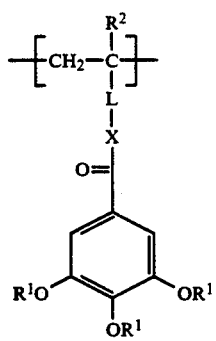

(I)

Wherein $R^1$ represents a hydrogen atom or some group which may be cleaved to give a hydrogen atom; $R^2$ represents hydrogen, an alkyl group, such as, methyl, ethyl, propyl, butyl and the like; or halogen such as chlorine, bromine and the like; and X and L together represent a divalent linking group to the polymer. The polymer may have a weight average molecular weight of $10^3 - 10^7$, more preferably $10^4 - 2 \times 10^6$. In formula (I), X represents a bond, and oxygen atom, or

where $R^3$ represents hydrogen, and alkyl or cycloalkyl group of 1-8 carbon atoms, or an aryl or heterocyclic group. L represents a bond or a divalent linking group.

DETAILED DESCRIPTION OF THE INVENTION

The invention thus contemplates polymeric $D_{ox}$ scavengers containing gallic acid fragments covalently bonded to polymer chains. These polymeric materials are advantageous in that they are readily prepared, show high activity toward $D_{ox}$, do not cause staining of the photographic element, do not crystallize or appreciably diffuse in coated film layers, are stable to the natural aging of the film, are not easily oxidized in air, and may be coated in silver halide emulsion layers without adverse effects. The polymers of the invention comprise at least 1 mol. % of a repeating unit represented by the formula (I) described above. In structure (I) $R^1$ represents a hydrogen atom or a group which can be cleaved to give a hydrogen atom. Examples of $R^1$ other than hydrogen include:

wherein $R^4$ constitutes a substituent of 1-8 carbon atoms, or more preferably of 1-5 carbon atoms, such as for example alkyl including methyl, ethyl, n-propyl, isopropyl, butyl, sec-butyl, tert-butyl, pentyl, neopentyl, hexyl, octyl and the like; aryl, such as phenyl, methyl phenyl, ethyl phenyl, and the like, cycloaliphatic, such as, cyclohexyl, cyclopentyl, methyl cyclohexyl and the like. $R^1$ may also include:

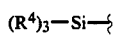

wherein $R^4$ is a substituent as described above, and where the three substituent on the silicon atom may be the same or different. In structure (I), X represents a bond, oxygen atom, or substituted nitrogen atom as described above. L represents a bond or a divalent linking group. An example of L is

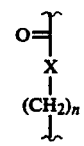

wherein n is between 2 and 10 and X is defined as above. The polymers of the invention may be water insoluble materials which are dispersed before coating in film layers, but preferably are latex polymers, or more preferably water dispersible or water soluble polymers. These require no dispersion preparation prior to being incorporated into the hydrophilic layers of the photographic elements, can be used in smaller amounts in that they do not require the use of a high-boiling solvent, and have improved properties in that they demonstrate increased activity compared to comparable dispersed scavengers. The polymeric oxidized developer scavenging agents in accordance with this invention were unexpected because active oxidized developer scavenging molecules are generally reactive toward free-radicals. Thus, an unsaturated group attached to scavenger moiety, such as a monomer corresponding to the polymer subunit represented by (I), cannot generally be polymerized by standard free-radical methods which are usually the most useful methods for preparing polymers of sufficient molecular weight to remain immobile in photographic elements.

One preferred embodiment of the invention is a copolymer containing at least 1 mol. % of subunits with structure (I) as well as subunits of structure (II) and (III), wherein $R^2$ and

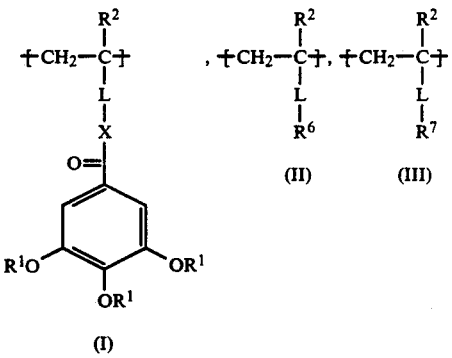

L are defined as above. $R^6$ is selected to be a group which is ionically charged or is ionizable in a photographic process. It is generally preferred that $R^6$ is chosen such that a homopolymer of subunits (II) would be water-soluble at some conditions of pH or ionic strength. Representative monomers which comprise subunits of type II are acrylic acid or its salts, methacrylic acid or its salts, styrenesulfonic acid or its salts, 2-acrylamido-2-methyl-1-propane sulfonic acid or its salts, 3-(dimethylaminopropyl) methacrylamide or its salts, 2-aminoethyl methacrylate or its salts, 6-acrylamidohexanoic acid, etc. $R^7$ represents a non-ionic or non-ionizable substituent, which, depending on L, may be hydrogen, a aliphatic substituent of 1-8 carbons or more preferably 1-6 carbons, or an aralkyl substituent of 1-10 carbons. $R^6$ or $R^7$ may contain additional substituents such as carbonyl groups, hydroxyl groups, or halogen groups. Representative monomers which comprise subunits of type (III) are simple acrylate or methacrylate esters, styrene and substituted styrenes, and acrylamide and N-substituted acrylamides and methacrylamides. By maintaining a proper balance of subunits (II) and (III), high scavenger activity and/or water-solubility of the polymer may be maintained because of the ionic nature of (II), while (III) may impart stability to a latex or immobility in the photographic layers for a solution polymer. This immobility presumably results from the higher molecular weight obtainable in polymers which contain subunit (III) or because of hydrophobic associations of the substituent $R^7$.

To prepare polymers of the invention, other comonomers may in general be copolymerized with (I) if they have at least one addition-polymerizable unsaturated bond. Examples include allyl compounds such as allyl esters (e g., allyl acetate, allyl caproate, etc.); vinyl ethers (e g., methyl vinyl ether, butyl vinyl ether, methoxyethyl vinyl ether, ethoxyethyl vinyl ether, chloroethyl vinyl ether, 1-methyl-2,2-dimethylpropyl vinyl ether, hydroxyethyl vinyl ether, diethylene glycol vinyl ether, dimethylaminoethyl vinyl ether, butylaminoethyl vinyl ether, benzyl vinyl ether, tetrahydrofurfuryl vinyl ether, etc.); vinyl esters (such as vinyl acetate, vinyl propionate, vinyl butyrate, vinyl isobutyrate, vinyl dimethyl propionate, vinyl ethyl butyrate, vinyl chloroacetate, vinyl dichloroacetate, vinyl methoxyacetate, vinyl phenyl acetate, vinyl acetoacetate, etc.); vinyl heterocyclic compounds (such as N-vinyl oxazolidone, N-vinylimidazole, N-vinylpyrrolidone, N-vinylcarbazole, vinyl thiophene, N-vinylethyl acetamide, etc.); styrenes (e.g., styrene, divinylbenzene, methylstyrene, dimethylstyrene, ethylstyrene, isopropylstyrene, sodium styrenesulfonate, potassium styrenesulfinate, butylstyrene, hexylstyrene, cyclohexylstyrene, benzylstyrene, chloromethylstyrene, trifluoromethylstyrene, acetoxymethylstyrene, methoxystyrene, 4-methoxy-3-methylstyrene, dimethoxystyrene, chlorostyrene, dichlorostyrene, trichlorostyrene, bromostyrene, iodostyrene, fluorostyrene, methyl vinylbenzoate ester, vinylbenzoic acid, etc.); crotonic acids (such as crotonic acid, crotonic acid amide, crotonate esters (e g., butyl crotonate, etc.)); vinyl ketones (e g., methyl vinyl ketone, etc); olefins (e g, dicyclopentadiene, ethylene, propylene, 1-butene, 5,5-dimethyl-1-octene, etc.); itaconic acids and esters (e.g., itaconic acid, methyl itaconate, etc.), other acids such as sorbic acid, cinnamic acid, methyl sorbate, citraconic acid, chloroacrylic acid mesaconic acid, maleic acid, fumaric acid, and ethacrylic acid; halogenated olefins (e.g., vinyl chloride, vinylidene chloride, ete ); unsaturated nitriles (e.g., acrylonitrile, etc.); acrylic or methacrylic acids and esters (such as acrylic acid, methyl acrylate, methacrylic acid, methyl methacrylate, ethyl acrylate, butyl acrylate, butyl methacrylate, 2-hydroxyethyl methacrylate, 2-acetoacetoxyethyl methacrylate, sodium-2-sulfoethyl acrylate, 2-aminoethylmethacrylate hydrochloride, glycidyl methacrylate, ethylene glycol dimethacrylate, etc.); and acrylamides and methacrylamides (such as acrylamide, methacrylamide, A-methylacrylamide, N-N-dimethylacrylamide, N-isopropylacrylamide, N-t-butylacrylamide, N-cyclohexylacrylamide, N-(3-aminopropyl)methacrylamide hydrochloride, N-(3-dimethylaminopropyl)methacrylamide hydrochloride, sodium N-(1,1-dimethyl-2-sulfoethyl)acrylamide, N-butylacrylamide, N-(1,1-dimethyl-3-oxobutyl)acrylamide, N-(2-carboxyethyl)acrylamide, 3-acrylamido-3-methylbutanoic acid, methylene bisacrylamide, etc.).

The polymers of the invention may have an average molecular weight of $10^3$–$10^7$, more preferably $10^4$–$2\times10^6$, with the preferred molecular weight dependent on the polymer structure. If the molecular weight is too low, the water soluble polymers may not be sufficiently immobile in the film, and if the molecular weight is too high, viscosity of the polymer solution may make it difficult to coat film layers of high quality. The latex polymers of the invention are not limited by the upper molecular weight limit given above, particularly if the latex contains ionic or ionizable components, such as carboxylic acid substituents. One example of this would be crosslinked latex containing a difunctional monomer such as ethylene glycol dimethacrylate, where the high molecular weight of the polymer does not impair the ability to coat film layers.

Polymers containing a subunit of structure (I) may be prepared by any of the techniques generally known in the art. For example, an unsaturated compound corresponding to (I) may be polymerized or copolymerized by any of the techniques known for the preparation of addition polymers from unsaturated monomers, as long as the technique is compatible with the chemical structure of the monomers. Free-radical addition polymerization is generally the most applicable method. The monomers may be polymerized in a solvent or solvent mixture which solubilizes the monomers and/or the polymer, using a free radical initiator. Also, emulsion polymerization may be employed, using a monomer corresponding to (I) combined with water-insoluble comonomers and possibly an organic cosolvent, in water with surfactant to emulsify the monomer mixture, and a free-radical initiator. This procedure generally produces a surfactant-stabilized latex. Alternatively, a preformed polymer with suitable reactive sites may be treated with a suitable gallic acid moiety, possibly using other chemical reagents which activate the polymer and/or the gallic acid moiety, so that a covalent bond is formed between the polymer and the gallic acid group resulting in the formation of a subunit of structure (I).

The scavengers of this invention can be used in the ways and for the purposes that $D_{ox}$ scavengers are employed in the art. They can be incorporated in a silver halide emulsion layer of the photographic element or in a separate layer of the element. When incorporated in a separate layer, that layer is preferably an interlayer between silver halide emulsion layers although it can be an undercoat layer coated below all of the silver halide emulsion layers or an overcoat layer coated above all of the silver halide emulsion layers. The scavengers can be prepared to contain water solubilizing groups which aid the scavengers in being compatible with the layer of the photographic element. The scavengers can also optionally be prepared to have ionizable, hydrophilic and/or non-ionizable hydrophobic groups which control the partitioning of the polymer between the aqueous and non-aqueous components of the film layer. This control the scavenger to compete effectively during processing with the dye-image forming compound for oxidized developer.

The amount of scavenger compound employed will depend upon the particular purpose for which the scavenger is to be used and the degree of scavenging desired. When the scavenger is used as a competitor, typically useful results are obtained using between 0.1–100 mol. %, or more preferably 1–30 mol. % relative to the amount of dye-image forming compound employed. When used as an interlayer scavenger, they are employed in an amount of between 1–1000 mol. %, or more preferably 10–100 mol. % relative to the amount of dye-image forming compound.

The scavenger can be incorporated in photographic elements by techniques known in the art. In the most preferred embodiments, the scavenger is water soluble, water dispersible, or is an aqueous latex. In these forms, the polymer may be combined directly with the other components of the layer in which the scavenger is incorporated. In certain embodiments, the scavenger is dissolved in a high boiling solvent, such as a water insoluble coupler solvent and then dispersed either in a silver halide emulsion layer or in a separate vehicle such as gelatin. Typical useful coupler solvents are moderately polar solvents such as tritolylphosphate, di-n-butylphthalate, diethyllauramide, 2,4-dipentylphenol, and the like. Typical vehicles are gelatin, and other hydrophilic colloids commonly employed in silver halide photographic elements. These vehicles are described in Research Disclosure, December 1978, Item No. 17643, Section IX.

The photographic elements of the present invention can be chromogenic monochrome elements comprising a support bearing a layer of the silver halide emulsion, or they can be multi-layer and/or multicolor elements. They can be designed for processing with separate solutions or for in-camera processing. Multicolor elements contain dye image forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsion or emulsions can be disposed as one or more segmented layers, e.g., as by the use of microvessels or microcells, as described in Whitmore U.S. Pat. No. 4,362,806 issued Dec. 7, 1982.

A preferred photographic element according to this invention comprises a support bearing at least one blue-sensitive silver halide emulsion layer having associated therewith a yellow image dye-providing material, at least one green-sensitive silver halide emulsion layer having associated therewith a magenta image dye-providing material and at least one red-sensitive silver halide emulsion layer having associated therewith a cyan image dye-providing material, the element containing a scavenger of this invention. The scavenger can be in an interlayer between silver halide emulsion layers sensitive to different regions of the visible spectrum, or it can be in a silver halide emulsion layer or in an interlayer between silver halide emulsion layers sensitive to the same region of the visible spectrum.

The elements of the present invention can contain additional layers conventional in photographic elements, such as overcoat layers, spacer layers, filter layers, antihalation layers, pH lowering layers (sometimes referred to as acid layers and neutralizing layers), timing layers, opaque reflecting layers, opaque light-absorbing layers and the like. The support can be any suitable support used with photographic elements. Typical supports include polymeric films, paper (including polymer-coated paper), glass and the like. Details regarding supports and other layers of the photographic elements of this invention are contained in Research Disclosure, December 1978, Item 17643, referred to above.

The light-sensitive silver halide emulsions employed in the photographic elements of this invention can include coarse, regular or fine grain silver halide crystals or mixtures thereof and can be comprised of such silver halides as silver chloride, silver bromide, silver bromo-iodide, silver chloro- bromide, silver chloroiodide, silver chlorobromo- iodide, and mixtures thereof. The emulsions can be, for example, tabular grain light-sensitive silver halide emulsions. The emulsions can be negative working or direct positive emulsions. They can form latent images predominantly on the surface of the silver halide grains or in the interior of the silver halide grains. They can be chemically and spectrally sensitized in accordance with usual practices. The emulsions typically will be gelatin emulsions although other hydrophilic colloids can be used in accordance with usual practices. Details regarding the silver halide emulsions are contained in Research Disclosure, Item 17643, December, 1978 and the references listed therein.

The photographic silver halide emulsions can contain other addenda conventional in the photographic art. Useful addenda are described, for example, in Research Disclosure, December 1978, Item 17643. Useful addenda include spectral sensitizing dyes and desensitizers, antifoggants, masking couplers, DIR couplers, DIR compounds, anti-stain agents, image dye stabilizers, absorbing materials such as filter dyes and UV absorbers, light scattering materials, coating aids, plasticizers and lubricants, and the like.

Depending upon the dye-image-providing material employed in the photographic element, it can be incorporated in the silver halide emulsion layer or in a separate layer associated with the emulsion layer. The dye-image-providing material can be any of a number known in the art, such as dye-forming couplers, bleachable dyes, dye developers and redox dye-releasers, and the particular one employed will depend on the nature of the element and the type of image desired.

Dye-image-providing materials employed with conventional color materials designed for processing with separate solutions are preferably dye-forming couplers; i.e., compounds which couple with oxidized developing agent to form a dye. Preferred couplers which form cyan dye images are phenols and naphthols. Preferred couplers which form magenta dye images are pyrazolones and pyrazolotriazoles. Preferred couplers which form yellow dye images are benzoylacetanilides and pivalylacetanilides.

Dye-image-providing materials useful in diffusion transfer film units contain a dye moiety and a monitoring moiety. The monitoring moiety, in the presence of an alkaline processing solution and as a function of silver halide development, is responsible for a change in mobility of the dye moiety. These dye-image-providing materials can be initially mobile and rendered immobile as a function of silver halide development, as described in U.S. Pat. No. 2,983,606. Alternatively, they can be initially immobile and rendered mobile, in the presence of an alkaline processing solution, as a function of silver halide development. This latter class of materials include redox dye-releasing compounds. In such compounds, the monitoring group is a carrier from which the dye is released as a direct function of silver halide development or as an inverse function of silver halide development. Compounds which release dye as a direct function of silver halide development are referred to as negative-working release compounds, while compounds which release dye as an inverse function of silver halide development are referred to as positive-working release compounds.

A preferred class of negative-working release compounds are the ortho or para sulfonamidophenols and naphthols described in U.S. Pat. Nos. 4,055,428 and 4,076,529. In these compounds the dye moiety is attached to a sulfonamido group which is ortho or para to the phenolic hydroxy group and is released by hydrolysis after oxidation of the sulfonamido compound during development.

A preferred class of positive-working release compounds are the nitrobenzene and quinone compounds described in U.S. Pat. No. 4,139,379. In these compounds the dye moiety is attached to an electrophilic cleavage group, such as a carbamate group, ortho to the nitro group or the quinone oxygen, and is released upon reduction of the compound by an electron donor compound contained in the element or the processing composition, unless the electron donor is oxidized during development.

The preferred developing agents to be used to develop the photographic elements of this invention are phenylenediamines, although other oxidized developing agents with the proper oxidation potential and reactivity may be scavenged by the polymer. These include some developing agents, which when used for certain applications, are referred to in the art as electron transfer agents. The particular developing agent employed will depend on the particular type of photographic element to be processed. Representative developing agents include: N,N-diethyl-p-phenylenediamine, 3-methyl-N,N-diethyl-p-phenylenediamine, 3-methoxy-N,N-diethyl-p-phenylenediamine, N,N,N',N'-tetramethyl-p-phenylenediamine.

The terms "non-diffusible", "non-wandering" or immobile used herein have the meaning commonly applied to the terms in photography and denote materials that for all practical purposes do not migrate or wander through organic colloid layers of a photographic element, such as gelatin, when the element is manufactured, stored, or processed in the usual manner. The terms "diffusible", "wandering" or mobile have the converse meaning and denote the materials having the property of diffusing effectively through the colloid layers of photographic elements under any of the above conditions.

Random copolymers having the following formulae are typical polymers containing a subunit represented by formula (I) set forth above. The molar ratio of the various monomer components present in the polymers is indicated by the numbered molar ratio compositions immediately following each formula:

Polymer Compositions

Example 1 and 2

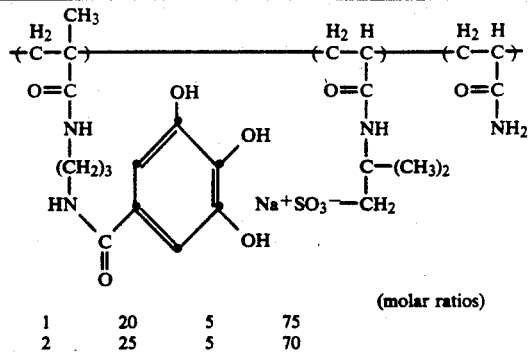

| | A | B | C |
|---|---|---|---|
| 1 | 20 | 5 | 75 |
| 2 | 25 | 5 | 70 |

(molar ratios)

Example 3 and 4

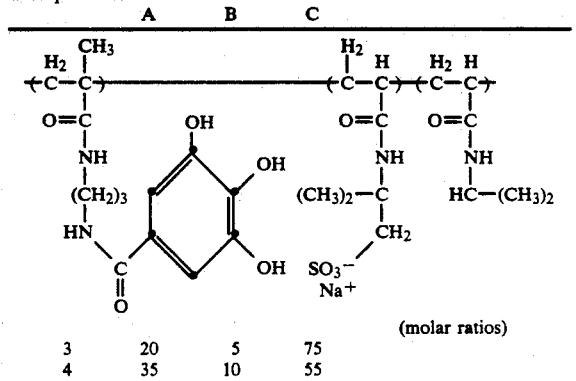

| | A | B | C |
|---|---|---|---|
| 3 | 20 | 5 | 75 |
| 4 | 35 | 10 | 55 |

(molar ratios)

Example 5–13

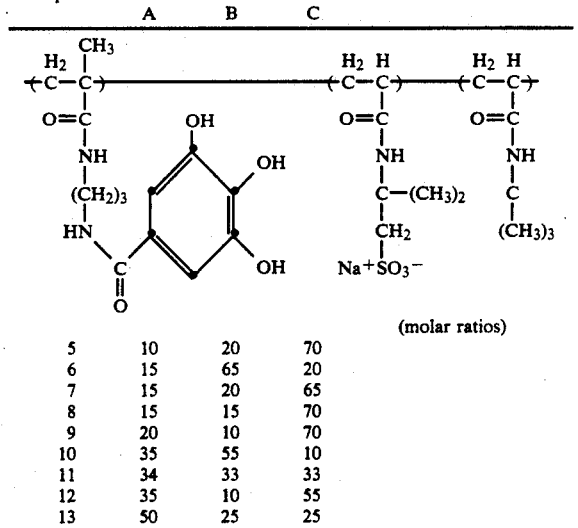

| | A | B | C |
|---|---|---|---|
| 5 | 10 | 20 | 70 |
| 6 | 15 | 65 | 20 |
| 7 | 15 | 20 | 65 |
| 8 | 15 | 15 | 70 |
| 9 | 20 | 10 | 70 |
| 10 | 35 | 55 | 10 |
| 11 | 34 | 33 | 33 |
| 12 | 35 | 10 | 55 |
| 13 | 50 | 25 | 25 |

(molar ratios)

Example 14

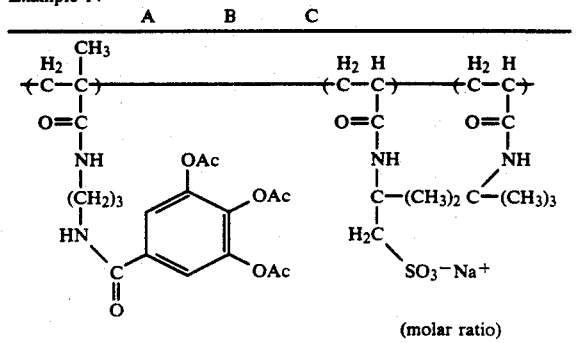

| A | B | C |
|---|---|---|

(molar ratio)

-continued

Polymer Compositions

| 14 | 15 | 20 | 65 |

Example 15 and 16

| | A | B | C |

[Chemical structure: terpolymer with methacrylate ester of N-(3,4,5-trihydroxybenzoyl)ethanolamine (A), 2-acrylamido-2-methylpropanesulfonate sodium salt (B), and t-butylacrylamide (C)]

(molar ratios)

| 15 | 34 | 33 | 33 |
| 16 | 15 | 20 | 65 |

Example 17

| | A | B | C |

[Chemical structure: terpolymer with methacrylate ester linked via (CH₂)₂-O-C(=O) to 3,4,5-trihydroxyphenyl (A), AMPS-Na (B), and t-butylacrylamide (C)]

(molar ratio)

| 17 | 12 | 26 | 62 |

Example 18 and 19

| | A | B | C |

[Chemical structure: terpolymer with methacrylamide of N-(3,4,5-trihydroxybenzoyl)propylamine (A), AMPS-Na (B), and N-pyridyl acrylamide (C)]

(molar ratios)

| 18 | 15 | 20 | 65 |
| 19 | 35 | 10 | 55 |

Example 20

| | A | B | C |

[Chemical structure: terpolymer with methacrylamide unit bearing 3,4,5-trihydroxybenzamide (A), acrylamide unit with (CH₃)₂C-SO₃⁻Na⁺ (B), and diacetone acrylamide type (C)]

(molar ratio)

| 20 | 15 | 20 | 65 |

-continued

Polymer Compositions

Example 21

| | A | B | C |

[Chemical structure: terpolymer with methacrylamide of N-(3,4,5-trihydroxybenzoyl)propylamine (A), AMPS-Na (B), and cyclohexyl acrylamide (C)]

(molar ratio)

| 21 | 25 | 20 | 55 |

Example 22

| | A | B | C |

[Chemical structure: terpolymer with methacrylamide of N-(3,4,5-triacetoxybenzoyl)propylamine (A), methacrylic acid type (B), and tetrahydrofuran-containing acrylate (C)]

(molar ratio)

| 22 | 13 | 12 | 75 |

Example 23 and 24

| | A | B |

[Chemical structure: copolymer with methacrylamide of N-(3,4,5-triacetoxybenzoyl)propylamine (A) and tetrahydrofuran-containing acrylate (B)]

(molar ratio)

| 23 | 13 | 87 |
| 24 | 5 | 95 |

Example 25, 26, and 27

| | A | B | C |

[Chemical structure: terpolymer with methacrylamide of N-(3,4,5-trihydroxybenzoyl)propylamine (A), AMPS-Na (B), and propyl-linked acrylamide (C)]

(molar ratio)

| 25 | 13 | 0 | 87 |
| 26 | 35 | 10 | 55 |
| 27 | 15 | 20 | 65 |

-continued
Polymer Compositions

Example 28

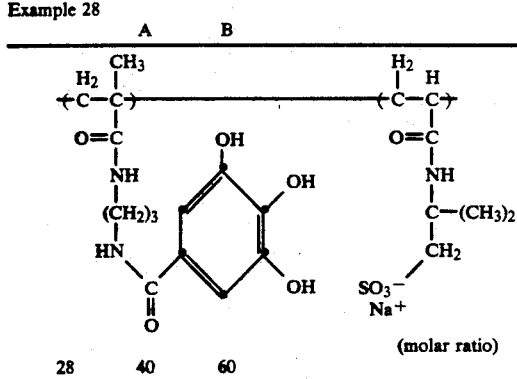

Example 29

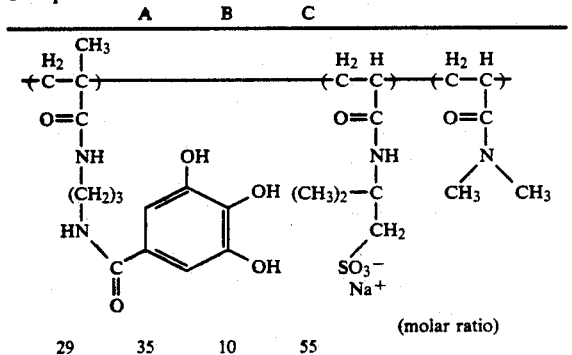

The water soluble, water dispersible or latex polymeric reducing agents in accordance with this invention demonstrate advantages over ballasted compounds, which advantages include the simplicity of the synthesis and the water-solubility or dispersibility that allows the polymeric compounds to be used directly without further preparation as in emulsified dispersion. Furthermore, the water soluble materials of the invention may be rendered non-diffusible in the photographic element by the molecular weight of the polymer and/or by the more hydrophobic components of the polymer, (i.e., the more hydrophobic subunits of structure (III)), which may aggregate with each other or associate with other film components. In some cases, the solution properties and dry physical properties of the polymers of this invention allow a portion of the vehicle in the layers of the photographic element containing the polymers to be reduced thereby reducing the total thickness of the layer and improving image sharpness in underlying layers of the photographic element.

When the polymers are placed in a light-sensitive layer containing silver halide emulsions, they are able to control the characteristic curve shape, reduce $D_{min}$ stain and improve the granularity. Alternatively, they can be incorporated in an interlayer between silver halide emulsion layers sensitive to different regions of the visible spectrum in order to prevent the diffusion of $D_{ox}$ between layers, thereby preventing wrong color dye formation. The identity and amount of the comonomers employed in the preparation of the polymers in accordance with this invention affects the observed photographic activity per mole of gallate subunits. Therefore, the composition can be varied to obtain the activity desired for a particular film system. The amount of polymeric reducing agents employed depends on the specific purpose for which the material is to be used and the degree of scavenging desired. The polymers of the invention, when used as a competitor, are employed in an amount of between 0.1–100 mol. %, or more preferably 1–30 mol. % relative to the amount of dye-image forming compound employed. When used as a scavenger, they are employed in an amount of between 1–1000 mol. %, or more preferably 10–100 mol. % relative to the amount of dye-image forming compound.

The invention will be further illustrated by the following examples:

Synthesis

Specific procedures for the preparation of materials of the invention are described below. Outlined is the preparation of monomers which correspond to the subunit structure (I), and specific procedures for the preparation of some of the polymers prepared from these monomers.

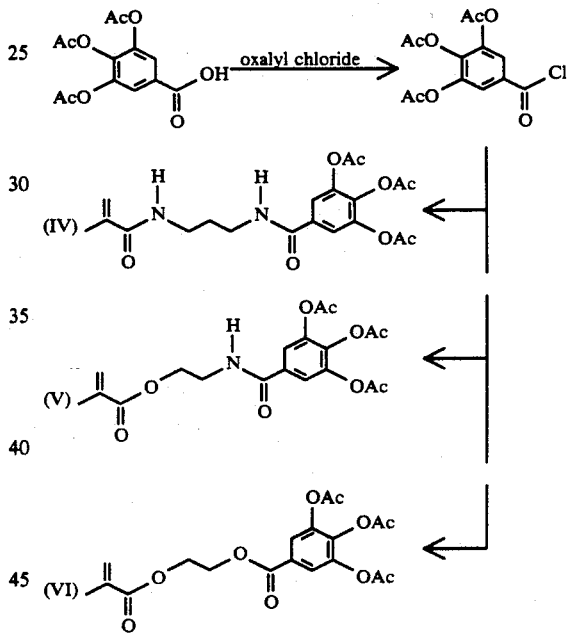

3,4,5-Triacetoxybenzoyl chloride: 3,4,5-Triacetoxybenzoic acid (296.23 g, 1 mol) was slurried in a 2 L flask in $CH_2Cl_2$ (1.0 L), and oxalyl chloride (113 mL, 1.3 mol) as added, followed by slow, dropwise addition of N,N-dimethylformamide (1.5 mL). After 2 hours at RT, gas evolution had ceased, and 3,4,5-triacetoxybenzoyl chloride was isolated by evaporation under reduced pressure.

N-(3-(methacrylamido)propyl-3,4,5-triacetoxybenzamide (IV): 3,4,5-Triacetoxybenzoyl chloride (1.0 mol) was dissolved in 1.2 L $CH_2Cl_2$ in a 3 neck 3 L flask, cooled to 0° C. To this was added 3-(aminopropyl)methacrylamide hydrochloride (178.66 g, 1 mol), followed by the slow addition of triethylamine (286 mL, 2.05 mol). After 3 hours, 1 L 2N HCl was added with vigorous stirring, the organic layer was isolated, washed with 500 mL saturated $NaHCO_3$ and 500 mL 1N HCl, dried over $MgSO_4$, and evaporated to remove the bulk of the solvent. The product was precipitated by pouring this solution slowly into a stirred flask of diethyl ether (1.5

L) containing seed crystals, and was isolated by filtration, washed with 3×350 mL ether, and dried in a stream of air overnight. Yield, 393.1 g pale yellow solid, 93.5%, mp 108°–110° C. $^1$H NMR (300 MHz, CDCl$_3$) and $^{13}$C NMR indicated the presence of a trace amount ($\approx$0.8 wt. %) of residual diethyl ether, and the product, δ1.61 (m, 5 lines, 2H), 1.93 (s, 3H), 2.23 (s, 6H), 2.24 (s, 3H), 3.28 (m, 4 lines, 2H), 3.36 (m, 4 lines, 2H), 5.30 (s, 1H), 5.73 (s, 1H), 6.90 (t, broad, 1H), 7.61 (s, 2H), 7.66 (t, broad, 1H). $^{13}$C {$^1$H} NMR (75.6 MHz, CDCl$_3$), δ18.43, 20.00, 20.37, 29.24, 35.88, 36.37, 119.75, 119.94, 132.43, 137.04, 139.45, 143.24, 165.23, 166.47, 167.60, 168.96. Anal., calcd for $C_{20}H_{24}N_2O_8$ C 57.14, H 5.75, N 6.66, found C 56.87, H 5.71, N 6.61.

2-(3,4,5-triacetoxybenzamido)ethyl methacrylate (V): 3,4,5-Triacetoxybenzoyl chloride (0.050 mol) was dissolved in 100 mL CH$_2$Cl$_2$ at 0° C. To this was added 2-aminoethyl methacrylate hydrochloride (8.28 g, 0.050 mol), followed by dropwise addition of triethylamine (14.63 mL, 0.105 mol). After 30 min, 100 mL 1N HCl was added with vigorous stirring. The organic layer was isolated, washed with saturated NaHCO$_3$ and 50 mL 1N HCl, dried over MgSO$_4$, and evaporated to give an oil, which crystallized rapidly after the addition of 50 mL diethyl ether. The product was isolated by filtration and vacuum dried. Yield, 17.97 g as a white solid, 88%. $^1$H NMR (300 MHz, CDCl$_3$), δ1.92 (s, 3H), 2.26 (s, 6H), 2.27 (s, 3H), 3.68 (m, 2H), 4.30 (t, 2H), 5.58 (m, 1H), 6.11 (s, 1H), 6.66 (t, broad, 1H), 7.51 (s, 2H). Anal., calcd for $C_{19}H_{21}N_1O_9$ C 56.02, H 5.20, N 3.44, found C 55.99, H 5.15, N 3.50.

2-(3,4,5-triacetoxybenzoyloxy)ethyl methacrylate (VI): 3,4,5-Triacetoxybenzoyl chloride (0.090 mol) was dissolved in 100 mL CH$_2$Cl$_2$ at 0° C. To this was added 2-hydroxyethyl methacrylate (11.75 g, 0.090 mol), followed by dropwise addition of triethylamine (13.9 mL, 0.10 mol). After addition was completed, the mixture was allowed to warm to RT and was stirred for 3 hours. 100 mL 0.5N HCl was added with vigorous stirring, the organic layer was isolated, washed with 50 mL saturated NaHCO$_3$ and 100 mL 0.5N HCl, dried over MgSO$_4$, and evaporated to yield a clear colorless fluid. Addition of ligroin (150 mL) and seeding caused crystallization, and the solid was isolated by filtration, washed with ligroin, and vacuum dried. Yield, 33.9 g as a white solid, 92%. Proton and carbon NMR indicated the presence of pure product, $^1$H NMR (300 MHz, CDCl$_3$), δ1.93 (s, 3H), 2.29 (s, 9H), 4.44, 4.55 (ab of m, 4H), 5.58 (m, 1H), 6.12 (s, 1H), 7.79 (s, 2H).

Preparation of polymer 7: N-t-butyl acrylamide (66.14 g, 0.52 mol), 2-acrylamido-2-methyl propane sulfonic acid, sodium salt (36.68 g, 0.16 mol) and N-(3-(methacrylamido)propyl)-3,4,5-triacetoxybenzamide (IV) (50.46 g, 0.12 mol) were dissolved in 640 mL 1:1 v:v methanol:water, and the solution was placed in a stirred 1 L 3-necked reaction flask at 60° C. under a nitrogen atmosphere. Azobis(isobutyronitrile)(1.32 g, 0.008 mol) was added, and the mixture was maintained at 60° C. for 7 hours. The resulting viscous solution was dialysed (10,000 Mw cutoff), yielding 1700 g clear solution, 7.09% solids (87% yield). $^1$H NMR (300 MHz, DMSO-d$_6$/D$_2$O) of a freeze-dried sample showed a single aromatic resonance at δ=6.79 and no signals attributable to acetate protective groups, indicating complete cleavage of the acetate esters. Inherent viscosity was measured in 0.1N LiCl in methanol at 25° C., c=0.256 g/dL; ηinh=0.72. Molecular weight determination, using low-angle laser light scattering (LALLS) in 0.1N LiBr in methanol, indicated $M_w$=9.68 ×10$^5$.

Preparation of polymer 9: N-t-butyl acrylamide (44.52 g, 0.35 mol), 2-acrylamido-2-methyl propane sulfonic acid, sodium salt (11.46 g, 0.05 mol) and N-(3-(methacrylamido)propyl)-3,4,5-triacetoxybenzamide (IV) (42.04 g, 0.20 mol) were dissolved in 400 mL 1:1 v:v methanol:water, and the solution was placed in a stirred 1 L 3-necked reaction flask at 60° C. under a nitrogen atmosphere. Azobis(isobutyronitrile)(0.82 g, 0.005 mol) was added, and the mixture was maintained at 60° C. for 7 hours. The resulting viscous solution was diafiltered (10,000 Mw cutoff, 7 turnovers), yielding 783 g of a translucent, water-dispersed material, 8.23% solids (75.6% yield). $^1$H NMR (300 MHz, DMSO-d$_6$/D$_2$O) of a freeze-dried sample was consistent with the monomer feed ratios, with complete cleavage of the aryl acetate groups. Inherent viscosity in 0.1N LiCl in methanol at 25° C., c=0.255 g/dL; ηinh=0.56.

Preparation of polymer 14: N-t-butyl acrylamide (8.27 g, 0.065 mol), 2-acrylamido-2-methyl propane sulfonic acid, sodium salt (4.58 g, 0.020 mol) and N-(3-(methacrylamido)propyl)-3,4,5-triacetoxybenzamide (IV) (6.31 g, 0.015 mol) were dissolved in 50 mL dimethylsulfoxide in a stirred 250 mL 3-necked reaction flask at 60° C. under a nitrogen atmosphere. Azobis(isobutyronitrile) (0.16 g, 0.001 mol) was added, and the mixture was maintained at 60° C. for 7 hours. The resulting viscous solution was dialysed (10,000 mw cutoff, 18 hours), yielding 217 g of a clear pale-yellow solution, 8.10% solids (92% yield). $^1$H NMR (300 MHz, DMSO-d$_6$/D$_2$O) of a freeze-dried sample was consistent with the monomer feed ratios, with nearly complete retention of the aryl acetate groups. Inherent viscosity in 0.1N; LiCl in methanol at 25° C., c=0.250 g/dL; ηinh=0.68.

Preparation of polymer 15: N-t-butyl acrylamide (4.19 g, 0.033 mol), 2-acrylamido-2-methyl propane sulfonic acid, sodium salt (7.56 g, 0.033 mol) and 2-(3,4,5-triacetoxybenzamido)ethyl methacrylate (V) (13.85 g, 0.034 mol) were dissolved in 80 mL 1:1 v:v methanol:water in a stirred 3-necked reaction flask at 60° C. under a nitrogen atmosphere. Azobis(isobutyronitrile)(0.080 g) was added. After 1 h, additional initiator (0.080 g) was added, and the mixture was maintained at 60° C. for 6 hours. The resulting viscous solution was dialysed (10,000 Mw cutoff), yielding 303 g clear solution, 5.84% solids (83% yield). $^1$H NMR (300 MHz, DMSO-d$_6$/D$_2$O) of a freeze-dried sample indicated complete cleavage of the aryl acetate groups.

Preparation of polymer 17: N-t-butyl acrylamide (7.63 g, 0.060 mol), 2-acrylamido-2-methyl propane sulfonic acid, sodium salt (5.73 g, 0.025 mol) and 2-(3,4,5-triacetoxybenzoyloxy)ethyl methacrylate (VI) (4.72 g, 0.0116 mol) were dissolved in 80 mL 1:1 v:v methanol:water in a stirred 3-necked reaction flask at 60° C. under a nitrogen atmosphere. Azobis(isobutyronitrile)(0.080 g) was added. After 30 min, additional initiator (0.080 g) was added, and the mixture was maintained at 60° C. for 6 hours. The resulting solution was dialysed (10,000 Mw cutoff), yielding 277 g clear solution, 4.50% solids (75% yield).

Preparation of polymer 23: Butyl acrylate (50.0 g, 0.39 mol), and N-(3-(methacrylamido) propyl)-3,4,5-triacetoxybenzamide (IV) (25.0 g, 0.060 mol) were dissolved in 50 mL methanol, and the resulting clear solution was added to a rapidly stirred solution of non-ionic surfactant (Olin 10G, 3.75 g) in 275 mL water at RT under a nitrogen atmosphere. The resulting emulsion was pumped over a period of 1 hour into a stirred 1 L reaction vessel at 80° C. containing water (400 mL), nonionic surfactant (Olin 10G, 3.75 g) and a water-soluble free-radical initiator (2,2'-azobis(2-amidinopropane) dihydrochloride, 0.75 g). After addition was complete, heating was maintained at 80° C. for 1 hour. The product was dialysed (10,000 MW cutoff) for 18 hours. Yield was 744 g of a translucent white, non-viscous latex, 8.31% solids. Inherent viscosity in THF at 25° C., c=0.252 g/dL; ηinh=0.40.

Preparation of polymer 24: Butyl acrylate (24.4 g, 0.19 mol), and N-(3-(methacrylamido) propyl)-3,4,5-triacetoxybenzamide (IV) (4.20 g, 0.010 mol) were combined with 110 mL ethyl acetate and azobis(isobutyronitrile)(0.16 g) in a vessel sealed with a septum. The vessel was purged with $N_2$ and heated to 60° C. with agitation for 24 h. Additional AIBN (0.16 g) was added and the mixture was heated for an additional 24 h. Yield 124.7 g solution, 22.6% solids. $^1H$ NMR of an evaporated sample showed no residual monomers and was consistent with the desired copolymer structure. Inherent viscosity in ethyl acetate at 25° C., c=0.238 g/dL; ηinh=0.44. The polymer in ethyl acetate solution was then dispersed in a gelatin solution containing surfactant, followed by removal of the ethyl acetate by evaporation before use.

EXAMPLE 1

Some materials of the invention were evaluated in a two-layer format consisting of an image layer and an overcoat. The image layer was coated on a cellulose triacetate film base and contained 1.7 g/m$^2$ gelatin, 1.2 g/m$^2$ (1.84 mmol/m$^2$) of image coupler A, 1.75 g per Ag mole of tetraazaindene, 0.82 g/m$^2$ of silver halide emulsion and a polymer of this invention or another scavenger as a comparative example, in the amount indicated in Table I, which is equivalent to 0.46 mmol/m$^2$). The silver halide emulsion was comprised of silver bromoiodide grains (6.3% iodide, 0.53 micron) which were green sensitized with dyes B and C noted below. The overcoat consisted of 2.2 g/m$^2$ of gelatin. The coatings were hardened with bisvinylsulfonylmethane at a level of 1.75% of the total gelatin. TX-200 in combination with Olin 10 G was used as surfactant in both layers at a level of 0.75% and 0.25% of the total gelatin respectively. The scavengers were blended in the melt from a water solution, aqueous dispersion, or oil-in-water dispersion, as made. Each sample was exposed using a 21 step tablet ranging from 0 to 3.0 density in steps of 0.15 with a 5500K illuminant for 0.02 seconds through a Wratten 8 filter. All of the exposed samples were processed through a standard Kodak E-6 process, a color reversal process, to be described later.

The efficacy of the scavengers was evaluated in several ways. A simple but somewhat deficient method, which has been employed in the prior art, is to compare the maximum optical density of cyan image dye generated from processing (at exposure step 21) compared to that of the control sample without reducing agent. Decreased density readings may indicate high reactivity of the competing scavenger toward $D_{ox}$. Each reducing agent's competition activity varies with the amount of dye formation, making it difficult to compare the activity of different scavengers at only one exposure level. Furthermore, it is often desirable to have the highest competitor activity in areas of low dye formation. Therefore, normalized dye optical density vs. exposure plots were generated by dividing the density value at each step by the maximum density value (i.e at step 21). Competitors of high activity will show decreased normalized density in areas of moderately high exposure in the toe region (i.e. steps 8 or 9). This decreased density is due to the efficient reaction of the scavenger with oxidized developer when only a small amount of oxidized developer is formed. The method of measuring only the maximum density may be misleading, especially in cases where the maximum density is limited to some degree by the amount of dye-image forming compound and not only by the amount of oxidized developer which is formed. In such cases, even a very active scavenger may not cause much decrease in maximum density. However, as an initial evaluation in some coating formats, changes in maximum density may be taken as an indication of scavenger activity.

In Table 1 is shown data on the activity of the scavengers of this invention and some comparison compounds. The ratio of the red $D_{max}$ of the experimental coatings to the red $D_{max}$ of the gelatin control is shown, as an indication of scavenger activity in areas of high dye formation. The activity in areas of low dye formation is shown for exposure steps 8 and 9, where the number shown is the difference between the normalized density of the gelatin control coating and the normalized density of the experimental coating at step 8 or 9. The normalized density of the gelatin control coating was 0.066 at step 8 and 0.106 at step 9. A scavenger which leads to a decrease in density in the toe exactly proportional to the decrease in $D_{max}$ will give a value of 0, while a scavenger with higher toe activity will give a positive value, and a scavenger with lower activity in the toe relative to the $D_{max}$ region will give a negative value.

For comparison, a commonly used scavenger, ballasted hydroquinone D as well as three ballasted gallate compounds F, G, and H were coated and tested in the same format. Compound D was prepared as an emulsified dispersion in gelatin solution without any organic solvent. Dispersions of the ballasted gallate compounds were prepared by dissolving each compound in 0.5X by weight of N,N-diethyldodecanamide and 2X by weight of ethyl acetate, followed by emulsifying in gelatin. From the data listed in Table 1, it can be seen that polymers of this invention are very active as competitors at $D_{max}$, and that many have good activity in the toe region. The activity of the polymers is dependent on the specific copolymer structure, so some of the polymers are more reactive than the comparison compounds, while some have lower activity in the toe and/or at $D_{max}$. However, many are more reactive than scavenger D and surprisingly more active than ballasted gallate compounds at equal molar laydown. This is especially apparent in areas of low dye formation, where ballasted gallates F and G actually cause an undesirable increase in the normalized dye density in the toe region. Comparison compound F also caused defects in the film coating due to crystallization of the compound.

Each sample also went through a Kodak E-6 MQ process (to be described later) to assure the changes in dye density were not a result of polymer-induced fog in the first development step of the reversal process. None of the polymers of the invention caused a measurable increase in fog.

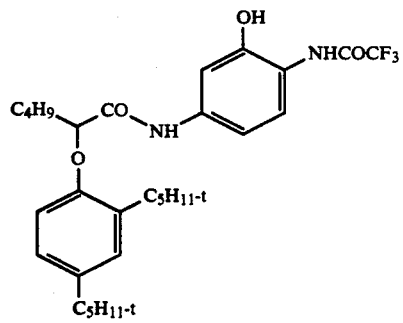
Coupler A
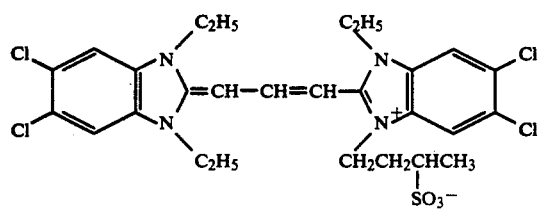
Dye B
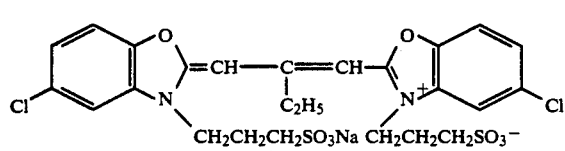
Dye C
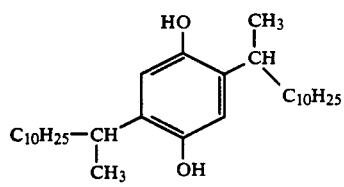
Scavenger D
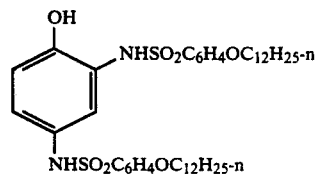
Scavenger E
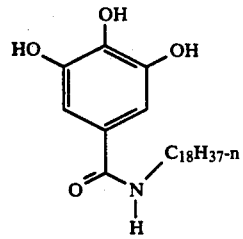
Scavenger F
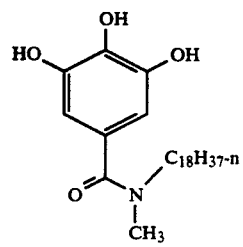
Scavenger G Scavenger H

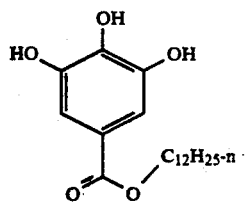

Coupler J

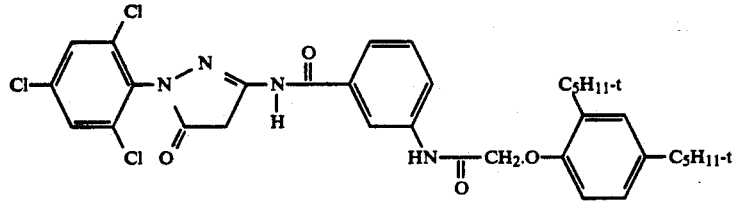

Coupler K

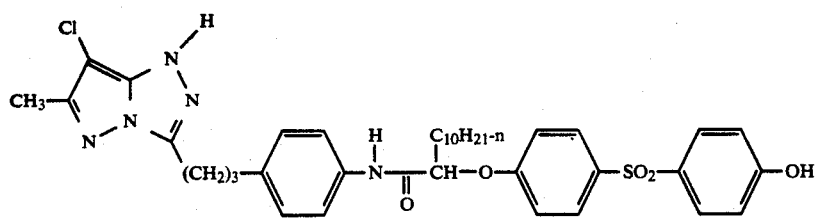

Coupler L

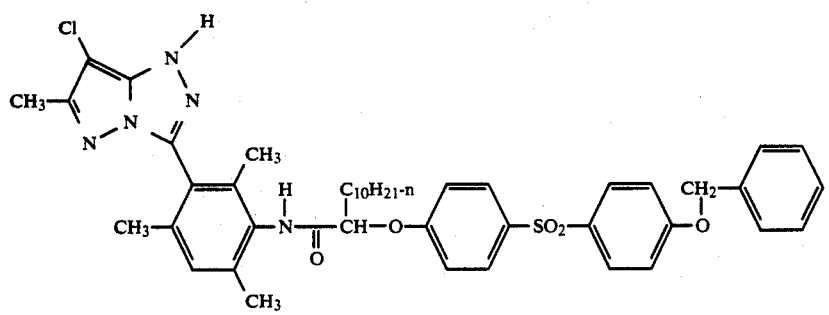

| E-6 MO Process (98.4F) | Kodak E-6 Process (98.4F) |
|---|---|
| 1st Developer (6 min.) | 1st Developer (6 min.) |
| Wash (2 min.) | Wash (2 min.) |
| Fix (4 min.) | Reversal Bath (2 min.) |
| Wash (4 min.) | Color Developer (6 min.) |
| | Conditioner (2 min.) |
| | Bleach (6 min.) |
| | Fix (2 min.) |
| | Wash (1 min.) |
| | Stabilizer (1 min.) |

The processing solutions used in each step had the following compositions:

| E-6 First Developer | |
|---|---|
| Water | 600.0 ml |
| Aminotris (methylenephosphonic acid), pentasodium salt, 40% solution | 1.41 g |
| Diethylenetriaminepentaacetic acid pentasodium salt, 40% solution | 6.26 g |
| Potassium sulfite, 45% solution | 66.10 g |
| Sodium bromide (anhydrous) | 2.34 g |
| Sodium thiocyanate | 1.00 g |
| Potassium iodide (anhydrous) | 4.50 mg |
| 4-Hydroxymethyl-4-methyl-1-phenyl-3-pyrazolidinone | 1.50 g |
| Potassium carbonate (anhydrous) | 14.00 g |
| Sodium bicarbonate (anhydrous) | 12.00 g |
| Potassium hydroquinone sulfonate | 23.40 g |
| Acetic acid | 0.58 g |
| Water to make | 1.005 L |
| pH @ 80 F 9.60 +/−0.05 | |

| E-6 Reversal Bath | |
|---|---|
| Water | 600.0 mL |
| Propionic acid | 11.90 g |
| Stannous chloride (anhydrous) | 1.65 g |
| p-Aminophenol | 0.50 mg |
| Soduim hydroxide, 50% solution | 9.92 g |
| Aminotris (methylenephosphonic acid), pentasodium salt, 40% solution | 21.10 g |
| Hyamine 1622, 50% solution | 10.00 mg |
| Water to make | 1.00 L |
| pH @ 80 F 5.75 +/−0.05 | |

| E-6 Color Developer | |
|---|---|
| water | 800.0 mL |
| Aminotris (methylenephosphonic acid), pentasodium salt, 40% solution | 6.68 g |
| Phosphoric acid, 75% solution | 17.40 g |
| Sodium bromide (anhydrous) | 0.65 mg |
| Potassium iodide (anhydrous) | 37.50 mg |
| Potassium hydroxide, 45% solution | 61.60 g |
| Sodium sulfite (anhydrous) | 6.08 g |
| Soduim metabisulfite | 0.50 g |

-continued

| | |
|---|---|
| Citrazinic acid | 0.57 g |
| KODAK Color Developing Agent CD-3 | 10.42 g |
| 2,2'-(Ethylenedithio)diethanol (3,6-dithia-1,8-octanediol) | 0.87 g |
| Acetic acid | 1.16 g |
| Sodium carboxymethylcellulose 7LF (Hercules) | 0.95 g |
| Sodium carboxymethylcellulose 7H3SF (Hercules) | 0.71 g |
| Water to make | 1.005 L |
| pH @ 80 F 11.75 +/−0.05 | |
| E-6 Conditioner | |
| Water | 800.0 mL |
| Potassium sulfite, 45% solution | 29.10 g |
| (Ethylenedinitrilo) tetraacetic acid | 8.00 g |
| Thioglycerol | 0.52 g |
| Water to make | 1.00 L |
| pH @ F 6.15 +/−0.10 | |
| E-6 Bleach | |
| Water | 500.0 mL |
| Potassium nitrate | 25.0 g |
| Ammonium bromide | 64.20 g |
| Ammonium ferric EDTA (1.56 M, pH 7.05, 44% wt.) (contains 10% molar excess EDTA, 3.5% wt.) | 284.00 g |
| Hydrobromic acid, 48% solution | 51.20 g |
| (Ethylenedinitrilo)tetraacetic acid | 4.00 g |
| Potassium hydroxide, 45% solution | 3.86 g |
| Water to make | 1.00 L |
| pH @ 80 F approx. 5.8 | |
| E-6 Fixer | |
| Water | 500.0 mL |
| Ammonium thiosulfate 56.5% ammonium thiosulfate, 4% ammonium sulfite) | 124.70 g |
| (Ethylenedinitrilo)tetraacetic acid | 0.59 g |
| Sodium metabisulfite | 7.12 g |
| Sodium hydroxide, 50% solution | 2.00 g |
| Water to make | 1.00 L |
| pH @ 80 F 6.60 +/−0.10 | |
| E-6 Stabilizer | |
| Water | 900.0 mL |
| RENEX 30 (ICI United States) (polyoxyethylene 12 tridecyl alcohol) | 0.14 g |
| Formaldehyde (37% solution, 12% Methanol) | 6.50 g |
| Water to make | 1.00 L |

TABLE 1

| Scavenger | Laydown (g/m$^2$) | Activity Step 21$^a$ | Activity Δ Step 8$^b$ | Activity Δ Step 9$^b$ |
|---|---|---|---|---|
| control | — | 1.000 | 0.000 | 0.000 |
| 1 invention | 0.28 | 0.810 | 0.00 | 0.00 |
| 2 invention | 0.28 | 0.820 | 0.011 | 0.021 |
| 3 invention | 0.36 | 0.811 | 0.010 | 0.012 |
| 4 invention | 0.25 | 0.823 | 0.015 | 0.018 |
| 5 invention | 0.75 | 0.722 | 0.000 | 0.002 |
| 6 invention | 0.66 | 0.718 | 0.001 | 0.006 |
| 7 invention | 0.53 | 0.728 | 0.006 | 0.019 |
| 8 invention | 0.51 | 0.894 | 0.000 | 0.000 |
| 9 invention | 0.39 | 0.712 | 0.000 | 0.001 |
| 10 invention | 0.31 | 0.838 | 0.015 | 0.029 |
| 11 invention | 0.29 | 0.806 | 0.015 | 0.025 |
| 12 invention | 0.25 | 0.803 | 0.057 | 0.094 |
| 13 invention | 0.21 | 0.816 | 0.012 | 0.022 |
| 14 invention | 0.58 | 0.770 | 0.004 | 0.012 |
| 16 invention | 0.52 | 0.703 | 0.005 | 0.017 |
| 18 invention | 0.55 | 0.747 | 0.000 | 0.000 |
| 20 invention | 0.61 | 0.780 | 0.103 | 0.159 |
| 21 invention | 0.38 | 0.866 | 0.062 | 0.103 |
| 23 invention | 0.57 | 0.842 | 0.000 | 0.006 |
| 25 invention | 0.57 | 0.821 | 0.062 | 0.101 |
| 27 invention | 0.53 | 0.766 | 0.010 | 0.013 |
| 29 invention | 0.24 | 0.843 | 0.013 | 0.016 |
| D comparison | 0.21 | 0.876 | 0.018 | 0.024 |
| F$^{(c)}$ comparison | 0.19 | 0.899 | −0.016 | −0.019 |
| G comparison | 0.20 | 0.899 | −0.015 | −0.020 |
| H comparison | 0.15 | 0.825 | 0.009 | 0.014 |

$^a$the value shown is:
($D_{max}^{(red)}$ competitor/$D_{max}^{(red)}$ gelatin control)
$^b$the value shown is:
($D_{(step\ n)}^{(red)}$gelatin control/$D_{(step\ 21)}^{(red)}$gelatin control) − ($D_{(step\ n)}^{(red)}$competitor/$D_{(step\ 21)}^{(red)}$competitor).
$^c$The dispersion of scavenger crystallized in the coating, causing severe defects in the film.

EXAMPLE 2

Coatings prepared from Example 1 were further tested for stability towards atmospheric oxygen. They were placed in a pressure vessel containing air at 4000 psi (27,580 Pa) and 50° C. and held for 72 hours, then followed by the exposure and standard Kodak E-6 process as described previously in Example 1. The maximum optical density of each coating was compared to that of the same coating without high pressure bomb treatment. The different in the optical density indicated the instability of the material to oxygen. The results given in Table 2 show that the polymeric materials are rather oxidatively stable. For comparison, a coating compound D showed not only a speed loss, but also a dramatic decrease in $D_{max}$, presumably due to the action of the products of the oxidation of D on the silver halide emulsion.

TABLE 2

| Compound No. | Laydown (g/m$^2$) | Dmax(Red) No Treatment | Dmax(Red) w/ High pressure bomb treatment | Δ Dmax (Red) |
|---|---|---|---|---|
| gel check | | 1.74 | 1.72 | −0.02 |
| 5 | 0.75 | 1.25 | 1.24 | −0.01 |
| 10 | 0.31 | 1.45 | 1.43 | −0.02 |
| 11 | 0.29 | 1.41 | 1.40 | −0.01 |
| 12 | 0.25 | 1.37 | 1.38 | 0.01 |
| 13 | 0.21 | 1.42 | 1.40 | −0.02 |
| D | 0.21 | 1.52 | 0.88 | −0.64 |

EXAMPLE 3

A different coating format was employed here to examine the diffusibility of the polymeric materials between layers in the photographic system. The test samples were prepared by coating the following layers on a cellulose triacetate film support in succession:

| Layer | Component | Coverage |
|---|---|---|
| (1) | Scavenger | 0.74 mmole/m$^2$ |
| | Gelatin | 0.87 g/m$^2$ |
| (2) | Gelatin | 1.74 g/m$^2$ |
| | Blue-sensitive silver bromoiodide emulsion as in Example 1 | 0.82 g/m$^2$ |
| | Image coupler A | 1.2 g/m$^2$ |
| | Tetraazaindene | 1.75 g/Ag mole |
| (3) | Gelatin | 1.1 g/m$^2$ |
| | Bisvinylsulfonylmethane | 1.75% of total gelatin |

TX-200 and 10G were used as surfactants in each layer at the level of 0.75% and 0.25% of the total gelatin, respectively. The samples were exposed to light and processed through standard Kodak E-6 process as described in Example 1.

Diffusion of materials in photographic system can take place during coating, during the film ageing process or during processing. In this coating format, the decrease in optical density of the processed sample indicates diffusion of the $D_{ox}$ scavenger into the emulsion layer where it competes with the image coupler for $D_{ox}$. In Table 3, the maximum optical density of each coating processed fresh as well as after incubation at 78° F./80% relative humidity for 2 weeks is listed. Compound E, a ballasted disulfamidophenol, is also tested here as a reference compound. Evidence shows that compound E does not diffuse in fresh coatings, yet has a tendency to wander on wet oven incubation. Many of the polymers in this invention are shown to be non-diffusible since the optical densities of fresh or incubated coatings stay unchanged from those of samples kept in 0° F. freezer, and the presence of the polymer in the imaging layer has been shown in Example 1 to cause a decrease in the maximum optical density.

TABLE 3

| Compound No. | Laydown (g/m2) | $D_{max}^{(Red)}$ 0° F./2 weeks check | $D_{max}^{(Red)}$ incubate @ 78° F./80% RH 2 weeks | $\Delta D_{max}^{(Red)}$ |
|---|---|---|---|---|
| gel check |  | 1.79 | 1.76 | −0.03 |
| 1 | 0.45 | 1.71 | 1.70 | −0.01 |
| 4 | 0.39 | 1.71 | 1.67 | −0.04 |
| 6 | 1.07 | 1.60 | 1.58 | −0.02 |
| 12 | 0.41 | 1.68 | 1.66 | −0.02 |
| 18 | 0.88 | 1.55 | 1.51 | −0.04 |
| 22 | 0.92 | 1.71 | 1.69 | −0.02 |
| 25 | 0.92 | 1.72 | 1.69 | −0.03 |
| D | 0.33 | 1.60 | 1.57 | −0.03 |
| E | 0.57 | 1.42 | 1.08 | −0.34 |

EXAMPLE 4

Processed samples from Table 1 were further checked for stain formation from $D_{ox}$ scavengers of this invention. The last column listed in Table 4 are status A densities for blue divided by red at step 21 (maximum density), a measure of the yellow stain normalized for the natural blue absorption of the cyan dye generated. As can be seen from the data, polymers of this invention cause minimal yellow stain.

TABLE 4

| Compound No. | Laydown g/m2 | $D_{max}^{(Blue)}/D_{max}^{(Red)}$ |
|---|---|---|
| Gel check |  | 0.090 |
| 1 | 0.28 | 0.125 |
| 2 | 0.28 | 0.121 |
| 3 | 0.36 | 0.133 |
| 4 | 0.25 | 0.131 |
| 5 | 0.75 | 0.134 |
| 6 | 0.66 | 0.146 |
| 7 | 0.53 | 0.148 |
| 8 | 0.51 | 0.130 |
| 9 | 0.39 | 0.146 |
| 10 | 0.31 | 0.126 |
| 11 | 0.29 | 0.130 |
| 12 | 0.26 | 0.131 |
| 13 | 0.21 | 0.127 |
| 14 | 0.58 | 0.129 |
| 16 | 0.52 | 0.144 |
| 18 | 0.55 | 0.152 |
| 20 | 0.61 | 0.110 |
| 21 | 0.15 | 0.117 |
| 23 | 0.57 | 0.120 |
| 25 | 0.57 | 0.116 |
| 27 | 0.53 | 0.144 |
| 29 | 0.24 | 0.124 |

TABLE 4-continued

| Compound No. | Laydown g/m2 | $D_{max}^{(Blue)}/D_{max}^{(Red)}$ |
|---|---|---|
| E | 0.36 | 0.315 |

EXAMPLE 5

Coated film samples were prepared using polymer 11 in a similar manner to the coatings of Example 1, except that the cyan dye image forming Coupler A was replaced with an equivalent molar amount of magneta dye image forming Coupler J, K, or L. As shown in Table 5, the polymers of the invention are active competitors in film systems containing a variety of image couplers.

TABLE 5[a]

| Coupler | Scavenger 11 (g/m²) | Activity Step 21 | Activity Δ Step 8 | Activity Δ Step 9 |
|---|---|---|---|---|
| J control | 0.00 | 1.000 | 0.000 | 0.000 |
| K control | 0.00 | 1.000 | 0.000 | 0.000 |
| L control | 0.00 | 1.000 | 0.000 | 0.000 |
| J invention | 0.29 | 0.786 | 0.038 | 0.042 |
| K invention | 0.29 | 0.969 | 0.047 | 0.063 |
| L invention | 0.29 | 0.611 | 0.011 | 0.035 |

[a]the values shown are calculated as in Table 1.

What is claimed is:

1. A light-sensitive photographic element comprising at least one hydrophilic colloid layer comprising a reducing agent comprising a polymer having at least 1 mol. % of a subunit represented by

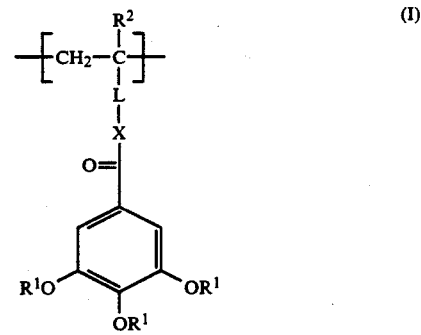

wherein $R^1$ represents a hydrogen atom or a group which may be cleaved to give a hydrogen atom, $R^2$ is hydrogen, an alkyl group or halogen atom, and X and L together represent a divalent linking group to the polymer.

2. A light-sensitive photographic element comprising at least one hydrophilic colloid layer of claim 1 wherein $R^1$ is hydrogen.

3. A light-sensitive photographic element comprising at least one hydrophilic colloid layer of claim 1 wherein $R^1$ is

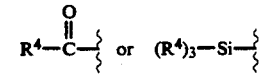

wherein $R^4$ is a substituent of 1 to 8 carbon atoms that may be the same or different.

4. A light-sensitive photographic element comprising at least one hydrophilic colloid layer of claim 1 wherein X is a bond, an oxygen atom or a substituted nitrogen atom.

5. A light-sensitive photographic element comprising at least one hydrophilic colloid layer of claim 1 wherein X is

where $R^3$ is hydrogen, alkyl, cycloalkyl, aryl or a heterocyclic group.

6. A light-sensitive photographic element comprising at least one hydrophilic colloid layer of claim 1 wherein L is

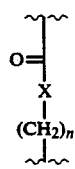

wherein X is a bond, an oxygen atom or a substituted nitrogen atom.

7. A light-sensitive photographic element comprising at least one hydrophilic colloid layer of claim 6 wherein X is

wherein R3 is hydrogen, an alkyl, cycloalkyl, aryl or heterocyclic group.

8. A light-sensitive photographic element comprising at least one hydrophilic colloid layer of claim 1 wherein the polymer has a molecular weight of $10^3$ to $10^7$.

9. A light-sensitive photographic element comprising at least one hydrophilic colloid layer of claim 1 wherein the polymer has a molecular weight $10^4$ to $2 \times 10^6$.

10. A light-sensitive photographic element comprising at least one hydrophilic colloid layer of claim 1 wherein the polymer is water soluble.

11. A light-sensitive photographic element comprising at least one hydrophilic colloid layer of claim 1 wherein the polymer is water dispersible.

12. A light-sensitive photographic element comprising at least one hydrophilic colloid layer of claim 1 wherein the polymer is an aqueous latex.

13. A light-sensitive photographic element comprising at least one hydrophilic colloid layer and a polymer having the subunits

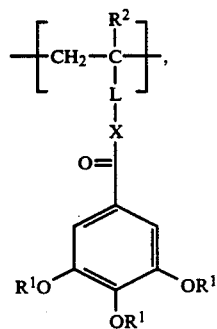

(I)

-continued

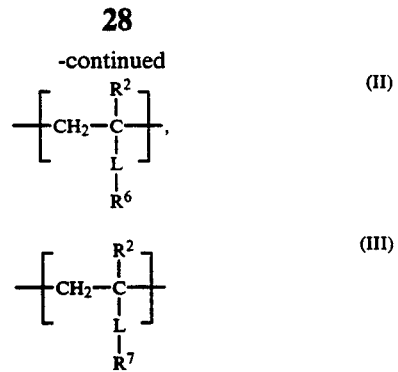

wherein the subunit of structure I is present in an amount of at least 1 mole percent, and at least one of the subunits II and III are present to form a copolymer wherein $R^1$ is a hydrogen atom or a group that when cleaved yields a hydrogen atom; $R^2$ is hydrogen, an alkyl group or halogen; X and L together represent a divalent linking group; $R^6$ is an ionically charged group or a group that is ionizable in a photographic process and $R^7$ is a non-ionic or non-ionizable group.

14. A light-sensitive photographic element comprising at least one hydrophilic colloid layer of claim 13 wherein $R^1$ is hydrogen.

15. A light-sensitive photographic element comprising at least one hydrophilic colloid layer of claim 13 wherein $R^1$ is

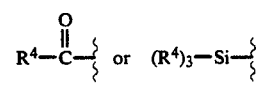

wherein $R^4$ is a substituent of 1 to 8 carbon atoms that may be the same or different.

16. A light-sensitive photographic element comprising at least one hydrophilic colloid layer of claim 13 wherein X is a bond, an oxygen atom or a nitrogen atom.

17. A light-sensitive photographic element comprising at least one hydrophilic colloid layer of claim 13 wherein X is

wherein $R^3$ is hydrogen, alkyl, cycloalkyl, aryl or a heterocyclic group.

18. A light-sensitive photographic element comprising at least one hydrophilic colloid layer of claim 13 wherein L is

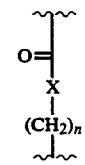

wherein X is a bond, an oxygen atom or a nitrogen atom, and where L may be different in each occurrence.

19. A light-sensitive photographic element comprising at least one hydrophilic colloid layer of claim 13 wherein X is

wherein R³ is hydrogen, an alkyl, cycloalkyl, aryl or heterocyclic group, and where L may be different in each occurrence.

20. A light-sensitive photographic element comprising at least one hydrophilic colloid layer of claim 13 wherein the polymer has a molecular weight of $10^3$ to $10^7$.

21. A light-sensitive photographic element comprising at least one hydrophilic colloid layer of claim 13 wherein the polymer has a molecular weight of $10^4$ to $2 \times 10^6$.

22. A light-sensitive photographic element comprising at least one hydrophilic colloid layer of claim 13 wherein the polymer is water soluble.

23. A light-sensitive photographic element comprising at least one hydrophilic colloid layer of claim 13 wherein the polymer is water dispersible.

24. A light-sensitive photographic element comprising at least one hydrophilic colloid layer of claim 13 wherein the polymer is an aqueous latex.

25. A light-sensitive photographic element comprising at least one hydrophilic colloid layer of claim 13 wherein subunit (II) is a moiety containing alpha-beta ethylenic unsaturation.

26. A light-sensitive photographic element comprising at least one hydrophilic colloid layer of claim 13 wherein subunit II is acrylic acid, salts of acrylic acid, methacrylic acid, salts of methacrylic acid, styrenesulfonic acid, salts of styrenesulfonic acid, 2-acrylamido-2-methyl-1-propane sulfonic acid, salts of 2-acrylamido-2-methyl-1-propane sulfonic acid, 3-(dimethylaminopropyl) methacrylamide, salts of 3-(dimethylaminopropyl) methacrylamide, 2-aminoethyl methacrylate, salts of 2-aminoethyl methacrylate, acrylamido hexanoic acid, or salts of acrylamido hexanoic acid.

27. A light-sensitive photographic element comprising at least one hydrophilic colloid layer of claim 13 wherein R⁷ is hydrogen, an aliphatic radical of 1 to 8 carbon atoms or an aralkyl radical of 1–10 carbon atoms.

28. The light-sensitive photographic element of claim 1 comprising at least one silver halide emulsion layer comprising the reducing agent.

29. The light-sensitive photographic element of claim 1 comprising at least one light sensitive silver halide emulsion layer and at least one non-light sensitive layer, the non-light sensitive layer comprising the reducing agent.

* * * * *